(12) United States Patent
Lin

(10) Patent No.: US 11,186,914 B2
(45) Date of Patent: Nov. 30, 2021

(54) WATER ELECTROLYSIS DEVICE

(71) Applicant: Hsin-Yung Lin, Shanghai (CN)

(72) Inventor: Hsin-Yung Lin, Shanghai (CN)

(*) Notice: Subject to any disclaimer, the term of this patent is extended or adjusted under 35 U.S.C. 154(b) by 65 days.

(21) Appl. No.: 16/108,729

(22) Filed: Aug. 22, 2018

(65) Prior Publication Data

US 2019/0062932 A1 Feb. 28, 2019

(30) Foreign Application Priority Data

Aug. 25, 2017 (CN) .......................... 201721073215.1

(51) Int. Cl.
| | |
|---|---|
| C25B 1/04 | (2021.01) |
| C25B 15/02 | (2021.01) |
| A61M 16/10 | (2006.01) |
| A61M 16/12 | (2006.01) |
| C02F 1/00 | (2006.01) |
| C02F 1/461 | (2006.01) |
| C25B 15/08 | (2006.01) |
| C25B 9/73 | (2021.01) |
| C25B 9/23 | (2021.01) |
| C25B 9/65 | (2021.01) |

(52) U.S. Cl.
CPC .............. *C25B 1/04* (2013.01); *A61M 16/10* (2013.01); *A61M 16/12* (2013.01); *C02F 1/008* (2013.01); *C02F 1/46104* (2013.01); *C02F 1/46109* (2013.01); *C25B 9/23* (2021.01); *C25B 9/73* (2021.01); *C25B 15/02* (2013.01); *C25B 15/08* (2013.01); *A61M 16/101* (2014.02); *A61M 2016/1035* (2013.01); *A61M 2205/053* (2013.01); *C02F 2001/46138* (2013.01); *C02F 2209/30* (2013.01); *C02F 2209/42* (2013.01); *C25B 9/65* (2021.01)

(58) Field of Classification Search
CPC ........ C25B 1/02–10; C25B 1/04; C25B 15/08
See application file for complete search history.

(56) References Cited

U.S. PATENT DOCUMENTS

| 2010/0206740 A1 | 8/2010 | Takeuchi et al. |
| 2011/0132748 A1 | 6/2011 | Haryu et al. |

(Continued)

FOREIGN PATENT DOCUMENTS

| CN | 103670808 A | * 3/2014 |
| CN | 205649716 | 10/2016 |

(Continued)

OTHER PUBLICATIONS

Office Action dated Nov. 26, 2019 for Australian Application No. 2018217292.

(Continued)

*Primary Examiner* — Nicholas A Smith

(57) ABSTRACT

A water electrolysis device for generating hydrogen gas includes a case, a power supplying unit, and an ion-exchange membrane electrolyzer. The case has a containing space including a bottom space and a top space. The bottom space is larger than the top space. The power supplying unit is configured in the bottom space for supplying power to operate the water electrolysis device. The ion-exchange membrane electrolyzer includes an ion-exchange membrane and a cathode, and the cathode generates hydrogen gas during which the ion-exchange membrane electrolyzer electrolyzes water.

18 Claims, 12 Drawing Sheets

(56) References Cited

U.S. PATENT DOCUMENTS

| | | | |
|---|---|---|---|
| 2011/0147202 A1 | 6/2011 | Haryu et al. | |
| 2012/0222955 A1* | 9/2012 | Takeuchi | C25B 1/12 |
| | | | 204/257 |
| 2015/0101601 A1* | 4/2015 | Lin | C25B 1/04 |
| | | | 128/202.26 |
| 2015/0190604 A1* | 7/2015 | Lin | A61M 16/122 |
| | | | 128/202.26 |
| 2016/0263341 A1 | 9/2016 | Lin | |
| 2018/0228995 A1 | 8/2018 | Lin | |
| 2018/0320275 A1 | 11/2018 | Lin | |

FOREIGN PATENT DOCUMENTS

| | | | |
|---|---|---|---|
| CN | 106906483 A | | 6/2017 |
| CN | 107041988 | | 8/2017 |
| JP | 2862808 B2 | | 3/1999 |
| JP | H08239788 | * | 3/1999 |
| JP | 2009005881 A | * | 1/2009 |
| JP | 2010189728 A | | 9/2010 |
| JP | 2016180177 A | | 10/2016 |
| JP | 2017012501 | | 1/2017 |
| RU | 148901 U1 | | 12/2014 |
| SU | 1411353 A1 | | 7/1988 |
| SU | 1461040 A1 | | 3/1995 |
| TW | 201723233 | | 7/2017 |
| TW | M554472 | | 1/2018 |
| WO | WO20150125981 | | 8/2015 |
| WO | WO2017024969 A1 | | 2/2017 |

OTHER PUBLICATIONS

Office Action dated Nov. 25, 2019 for Indian Application No. 201824030728.
Extended Search Report dated May 15, 2019 for European Application No. 18189192.0.
Office Action dated Aug. 6, 2019 for Canadian Application No. 3,015,215.
Search Report and Written Opinion dated Jan. 14, 2019 for Singapore Application No. 10201807060V.
Search Report and Written Opinion for Singapore Application No. 10202000541X, dated Jun. 23, 2020.

* cited by examiner

WATER ELECTROLYSIS DEVICE

CROSS-REFERENCE TO RELATED APPLICATIONS

This application claims the priority benefit of Chinese Application Serial No. 201721073215.1 filed Aug. 25, 2017 the disclosure of which is incorporated herein by reference.

BACKGROUND OF THE INVENTION

1. Field of the Invention

The present invention relates to a water electrolysis device, and more specifically, to a water electrolysis device that outputs hydrogen gas and oxygen gas on the same side of the electrolyzer.

2. Description of the Prior Art

As people have always been paying much attention on health developments, many developments in medical technology are often targeted on treating diseases and prolonging human life. Most of the treatments in the past are passive, which means that the disease is treated only when it occurs. The treatments include operations, medication treatments, radiation therapies, or even medical treatments for cancer. However, in recent years, most of the researches from medical experts are gradually moving towards preventive medical methods, such as research on healthy food, screening and the prevention of inherited diseases, which actively prevents diseases from occurring in the future. Due to the focus of the prolongation of human life, many anti-aging and anti-oxidation technologies including skin care products and anti-oxidation food/medicine are gradually being developed and have becoming increasingly popular to the general public.

Studies have found that there are instable oxygen species (O+), also known as free radicals, in the human body. The free radicals which are usually generated due to diseases, diet, environment and one's lifestyle can be excreted in the form of water by reacting with the inhaled hydrogen. With this method, the amount of free radicals in the human body can be reduced, thereby restoring the body condition from an acidic state to an alkaline state, achieving an anti-oxidation, anti-aging and beauty health effect, and even eliminating chronic diseases. Furthermore, there are also clinical experiments showing that patients who need to inhale a high concentration of oxygen for an extended period of time would experience lung damage, but it could be ameliorated by inhaling hydrogen In order to improve the effect of inhaling hydrogen gas, increasing the time of inhaling hydrogen gas is an effective way to improve the efficiency. In general, the conventional water electrolysis device is relatively bulky, and it is hard for a person to have enough time to inhale hydrogen gas by staying next to the conventional water electrolysis device during daily activities. Therefore, inhaling hydrogen gas during sleep time could be an effective way. However, as mentioned above, the conventional water electrolysis device is relatively bulky, how to reduce the volume of the water electrolysis device and to maintain sufficient hydrogen gas production are the problems that must be solved.

In addition to the health care mentioned above, the use of hydrogen gas can also be used to generate an oxyhydrogen flame for heating or combustion, and to remove engine carbon deposits and the like. In general, hydrogen gas is generated by the electrolyzing water in the electrolyzer; however, it is easy to cause high temperature during the process of electrolyzing water. In order to avoid gas explosion, the traditional hydrogen-oxygen electrolyzer is mostly air-cooled; namely, using a fan to cool down. However, if a trouble occurs on the fan, it will cause the temperature of the hydrogen-oxygen electrolyzer to rise and result in the danger of gas explosion. Furthermore, the hydrogen-oxygen mixed gas generated after electrolyzing water through the electrolysis device usually includes electrolyte, which is not suitable for human beings to inhale directly. At the same time, there is a problem of electrolyte consumption during the electrolysis process.

SUMMARY OF THE INVENTION

The present invention is to provide a water electrolysis device including a case, a power supplying unit and an ion-exchange membrane electrolyzer. The case includes a base and a side wall. A containing space is formed in the base and the side wall. The containing space includes a bottom space and a top space, and the bottom space is larger than the top space. The power supplying unit is configured in the bottom space of the case for supplying power to the water electrolysis device. The ion-exchange membrane electrolyzer is configured in a non-central position of the case, and includes a cathode. The cathode generates hydrogen gas during which the ion-exchange membrane electrolyzer electrolyzes water.

In one embodiment of the present invention, the ion-exchange membrane electrolyzer includes a first side, a second side, an ion-exchange membrane, an anode, an oxygen output tube and a hydrogen output tube. The ion-exchange membrane is configured between the anode chamber and the cathode chamber. When the ion-exchange membrane electrolyzer electrolyzes water, the anode generates oxygen gas. The oxygen output tube is used for outputting oxygen gas, and the cathode output tube is used for outputting hydrogen gas. The first side is close to the side wall, and both of the oxygen gas and the hydrogen gas are outputted from the second side of the ion-exchange membrane electrolyzer.

In one embodiment of the present invention, the anode is configured between the ion-exchange membrane and the second side, and the cathode is configured between the ion-exchange membrane and the first side. The oxygen output tube extends from the position between the ion-exchange membrane and the second side to the second side and passes through the second side. The hydrogen output tube extends from the position between the ion-exchange membrane and the first side to the second side and passes through the second side.

In one embodiment of the present invention, the anode is configured between the ion-exchange membrane and the first side, and the cathode is configured between the ion-exchange membrane and the second side. The oxygen output tube extends from the position between the ion-exchange membrane and the first side to the second side and passes through the second side. The hydrogen output tube extends from the position between the ion-exchange membrane and the second side to the second side and passes through the second side.

In one embodiment of the present invention, the anode chamber includes an anode sealing plate, an anode conductive plate and an anode external plate. The oxygen output tube passes through the anode external plate, the anode conductive plate and the anode sealing plate. The cathode chamber includes a cathode sealing plate and a cathode conductive plate. The hydrogen output tube passes through the anode external plate, the anode conductive plate, the anode sealing plate and the cathode sealing plate, wherein oxygen gas and hydrogen gas are outputted on the same side of the ion-exchange membrane electrolyzer.

In one embodiment of the present invention, the ion-exchange membrane electrolyzer further includes a water supplying pipe which is configured on and passes through the anode external plate, the anode conductive plate and the anode sealing plate to connect the anode chamber and a water tank. The water from the water tank flows into the anode chamber through the water supplying pipe to replenish the water in the anode chamber.

In one embodiment of the present invention, the water electrolysis device further includes an air supplying tube, a fan and an air pump. The air supplying tube is connected to the hydrogen output tube to receive hydrogen gas. The fan draws air from the environment outside the water electrolysis device into the water electrolysis device. The air pump guides the air into the air supplying tube to mix the air with hydrogen gas to dilute the volume concentration of hydrogen gas in the air supplying tube.

In one embodiment of the present invention, the air pump is connected with the air supplying tube by an air supplying interface. The air supplying tube has a first flow direction. The air supplying interface has a second flow direction. The first flow direction points to the upper portion of the water electrolysis device, and the second flow direction points to the air supplying tube. A lead angle is formed between the first flow direction and the second flow direction, wherein the lead angle is preferably between 25 to 45 degrees. The shape of the connecting position with the lead angle is made as an arc lead angle, so as to guide the air into the air supplying tube from the air supplying interface.

In one embodiment of the present invention, the water electrolysis device further includes an atomizing/volatile gas mixing tank which is connected to the air supplying tube and receives the diluted hydrogen gas. The atomizing/volatile gas mixing tank selectively generates an atomizing gas and mixes it with hydrogen gas to form a health gas, wherein the atomizing gas is one or a combination selected from a group consisting of water vapor, atomizing potions and volatile essential oil.

In one embodiment of the present invention, the water electrolysis device further includes a hydrogen concentration detector which is coupled to the air supplying tube for detecting whether the volume concentration of hydrogen gas in the air supplying tube is within a range from a first predetermined value to a second predetermined value. The hydrogen concentration detector generates a first warning signal when the detected volume concentration of hydrogen gas is higher than the first predetermined value. The water electrolysis device further includes a controller which is coupled to the hydrogen concentration detector and the ion-exchange membrane electrolyzer. The controller generates a start command to start up the air pump when receiving the first warning signal.

In one embodiment of the present invention, the hydrogen concentration detector generates a second warning signal when the detected volume concentration of the hydrogen gas is higher than the second predetermined value; and, the controller generates a stop command to stop the ion-exchange membrane electrolyzer when receiving the second warning signal. The first predetermined value is 4%, the second predetermined value is 6%, and the range is 4%~6%.

In one embodiment of the present invention, the water electrolysis device further includes a water level detecting device for detecting the amount of water in the water tank.

In one embodiment of the present invention, the volume of the water electrolysis device is less than 8.5 L, and a hydrogen gas generating rate of the water electrolysis device is located in a range between 120 ml/min and 600 ml/min.

In one embodiment of the present invention, the power supplying unit of the water electrolysis device includes a high power output and a low power output, wherein the electric power outputted by the low power output is equal to or less than half of that outputted by the high power output. The high power output outputs a first voltage and a first current. The low power output outputs a second voltage and a second current. The first voltage is less than the second voltage. The first current is greater than the second current.

The present invention further provides another water electrolysis device including a case and an ion-exchange membrane electrolyzer. The case includes a base and a side wall. The ion-exchange membrane electrolyzer includes a first side, a second side, an ion-exchange membrane, a cathode, an anode, an oxygen output tube and a hydrogen output tube. The ion-exchange membrane is configured between the anode and the cathode. When the ion-exchange membrane electrolyzer electrolyzes water, the cathode generates hydrogen gas, and the anode generates oxygen gas. The oxygen output tube is configured for outputting oxygen gas. The hydrogen output tube is configured for outputting hydrogen gas. The first side is close to the side wall, and both of oxygen gas and hydrogen gas are outputted from the second side of the ion-exchange membrane electrolyzer.

In another embodiment of the present invention, the anode is configured between the ion-exchange membrane and the second side, and the cathode is configured between the ion-exchange membrane and the first side. The oxygen output tube extends from the position between the ion-exchange membrane and the second side to the second side and passes through the second side. The hydrogen output tube extends from the position between the ion-exchange membrane and the first side to the second side and passes through the second side.

In another embodiment of the present invention, the anode is configured between the ion-exchange membrane and the first side, and the cathode is configured between the ion-exchange membrane and the second side. The oxygen output tube extends from the position between the ion-exchange membrane and the first side to the second side and passes through the second side. The hydrogen output tube extends from the position between the ion-exchange membrane and the second side to the second side and passes through the second side.

Through the ion-exchange membrane electrolyzer with hydrogen gas and oxygen gas outputted on the same side, the water tank, the gas-water separation tank, and the air supplying tube and the like configured in a case with a limited volume, the present invention uses the containing space in the case as much as possible while maintaining sufficient hydrogen gas production, and the use of the fan and the air pump are also based on low noise. Therefore, the present invention actually provides a water electrolysis device with effective space arrangement, small volume, low noise and suitable for placement around the user.

BRIEF DESCRIPTION OF THE APPENDED DRAWINGS

Figure 6:
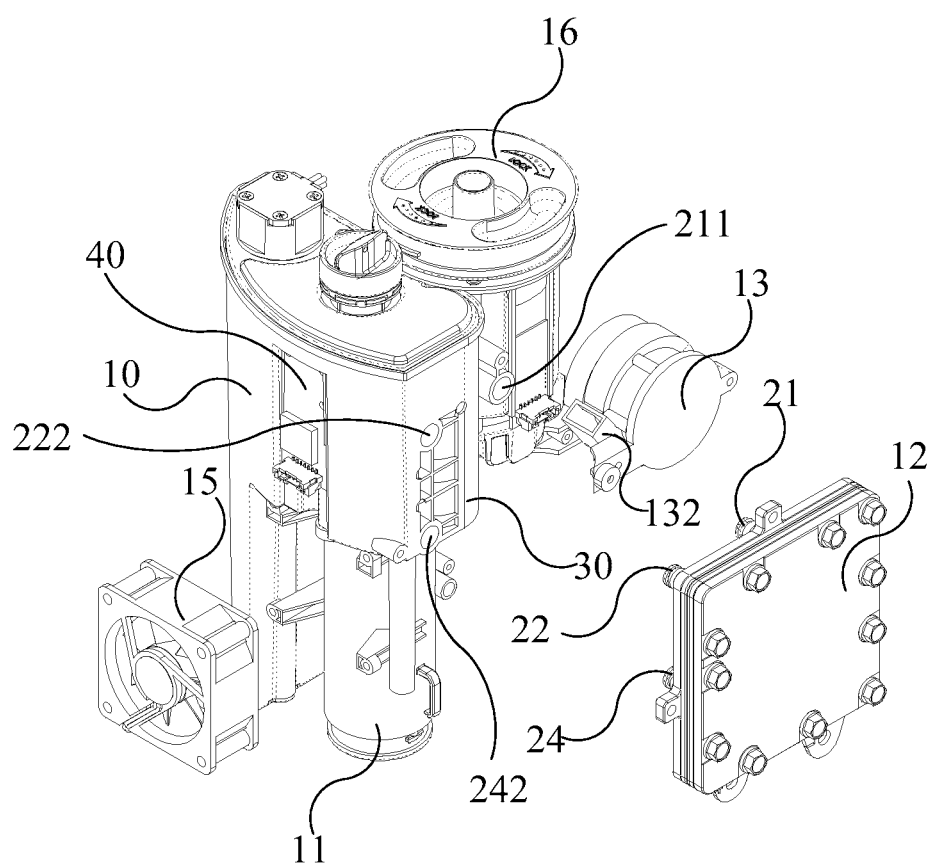
FIG. 6 is an exploded diagram illustrating the water electrolysis device according to an embodiment of the present invention.
Figure 7A:
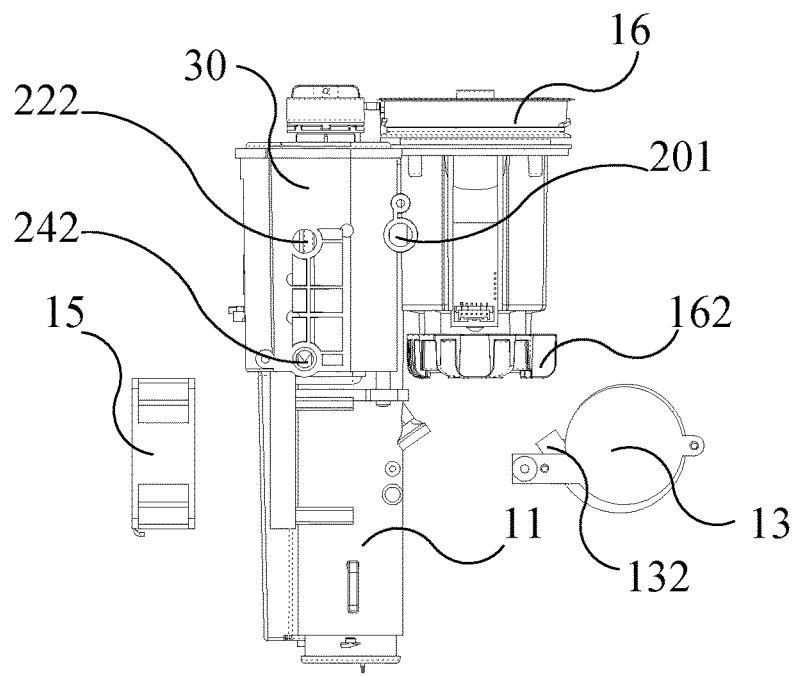
Figure 7B:
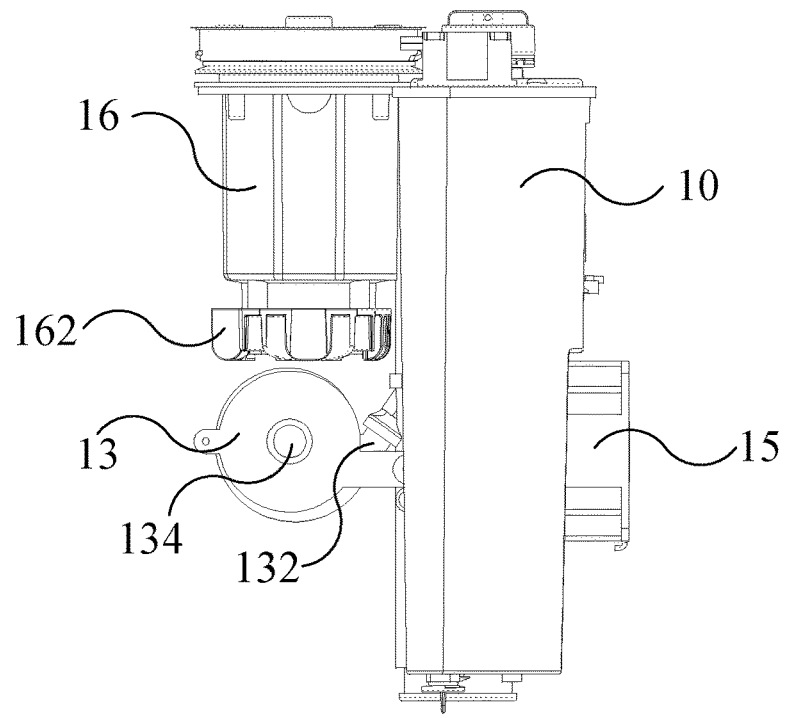

FIG. 7A and FIG. 7B respectively are an exploded diagram and an assembly diagram illustrating the water electrolysis device in FIG. 6 from another perspective.

Figures 8A, 8B:
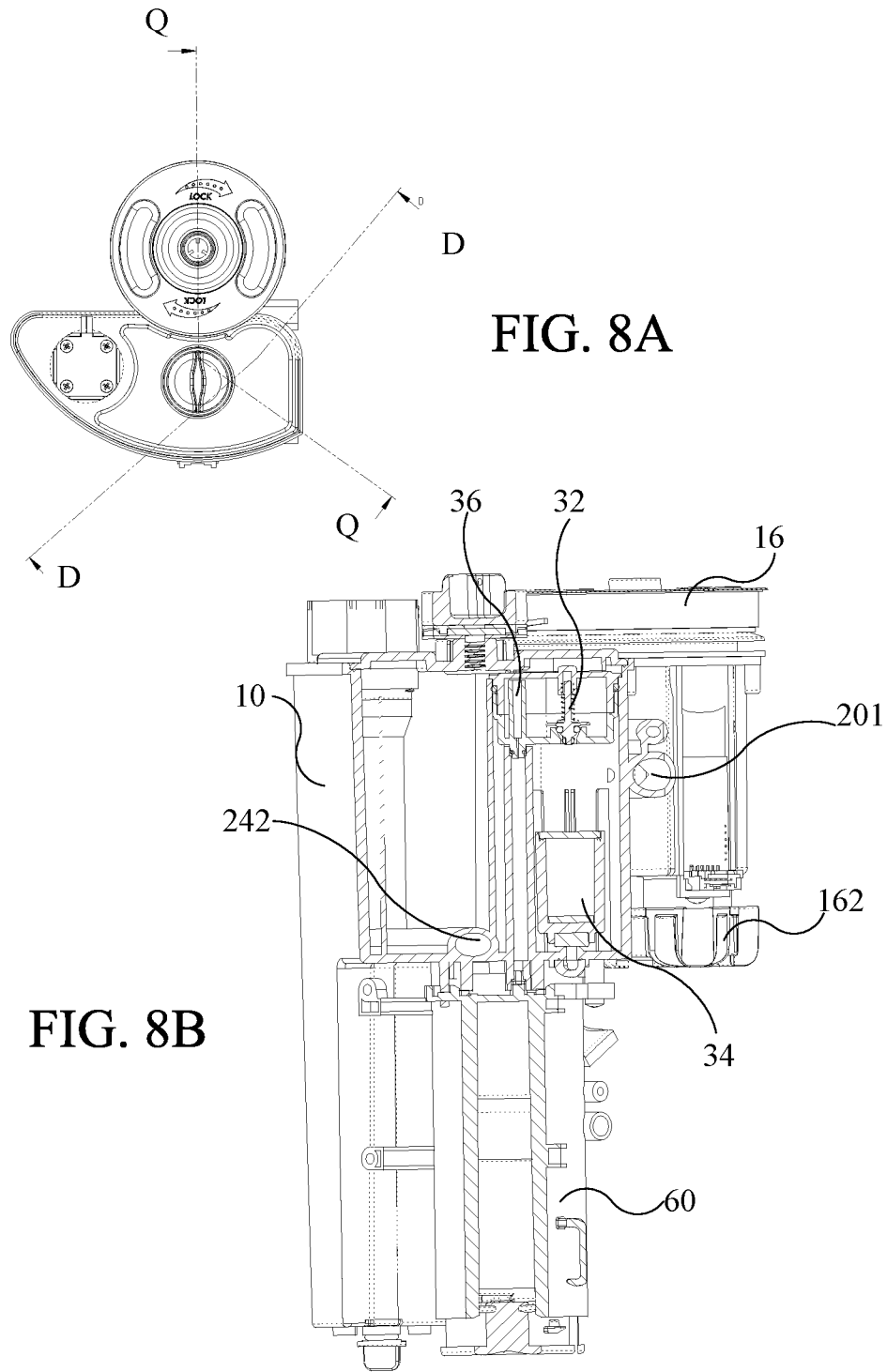

FIG. 8A is a top view diagram illustrating a water electrolysis device according to an embodiment of the present invention.

FIG. 8B is a sectional view illustrating the water electrolysis device along the line D-D in FIG. 8A.

Figure 9:
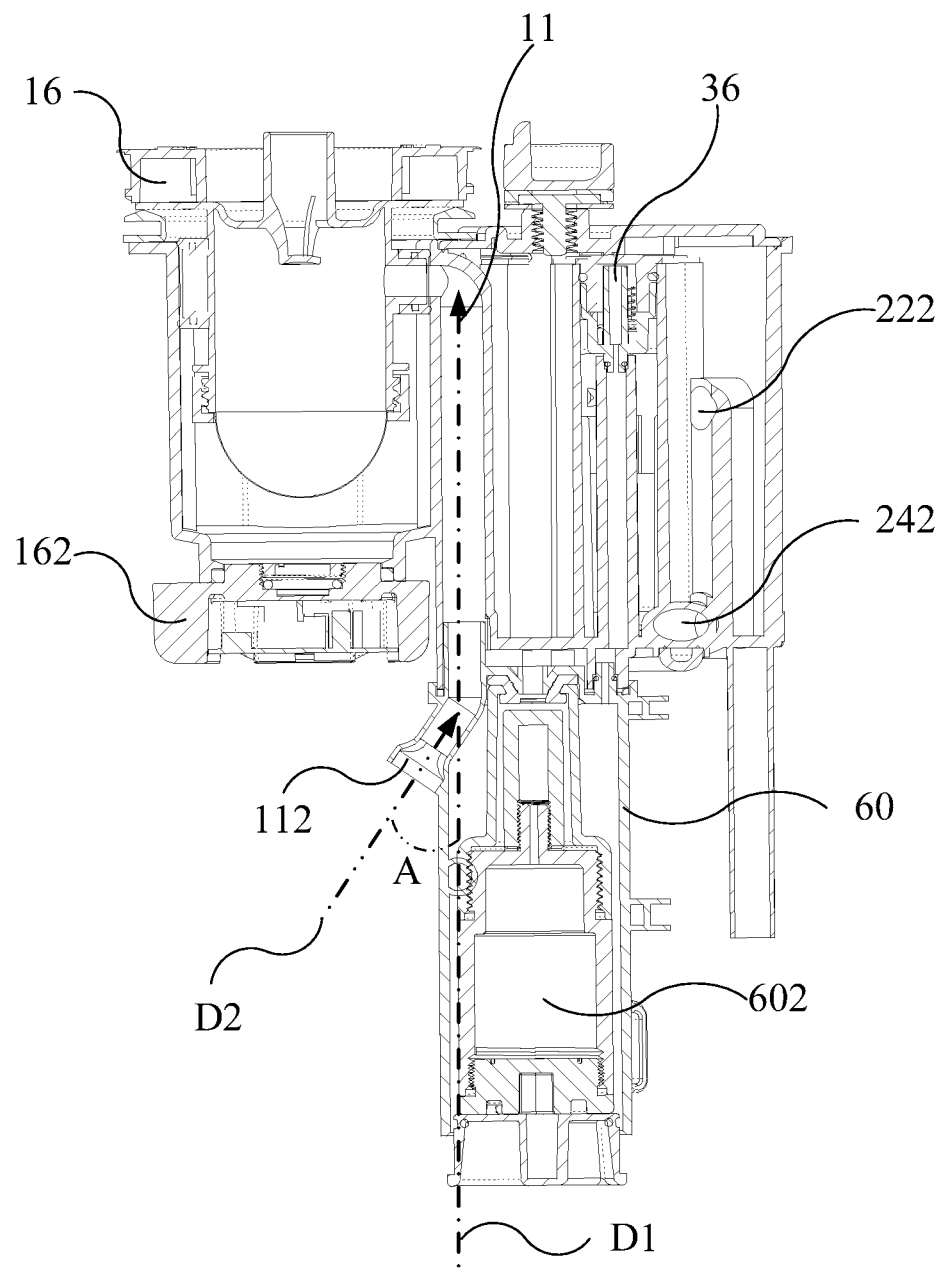

FIG. 9 is a sectional schematic diagram illustrating the water electrolysis device along the line D-D in FIG. 8A.

Figure 10:
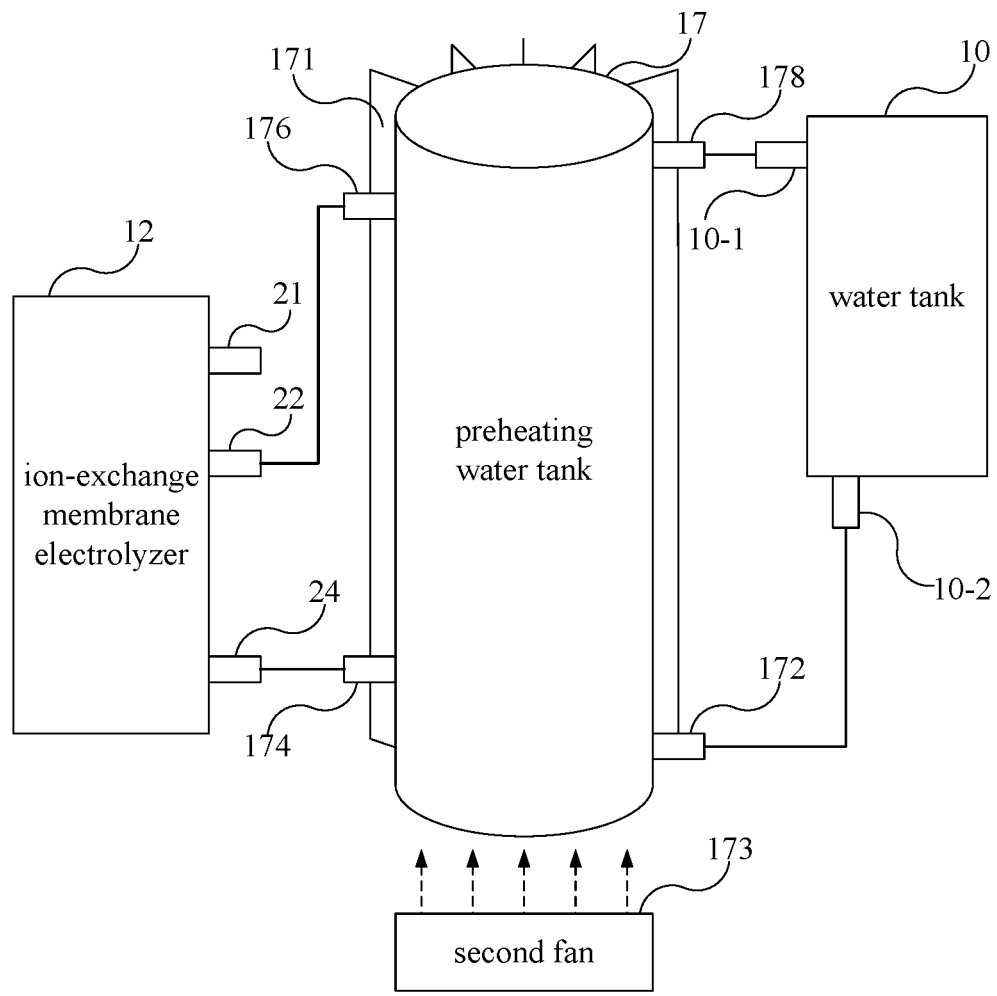

FIG. 10 is a schematic diagram illustrating a water electrolysis device according to another embodiment of the present invention.

The advantages, spirits and features of the present invention will be explained and discussed in detail by way of the embodiments and with reference of the diagrams.

DETAILED DESCRIPTION OF THE INVENTION

For the sake of the advantages, spirits and features of the present invention can be understood more easily and clearly, the detailed descriptions and discussions will be made later by way of the embodiments and with reference of the diagrams. It is worth noting that these embodiments are merely representative embodiments of the present invention, wherein the specific methods, devices, conditions, materials and the like are not limited to the embodiments of the present invention or corresponding embodiments.

Figure 1A:
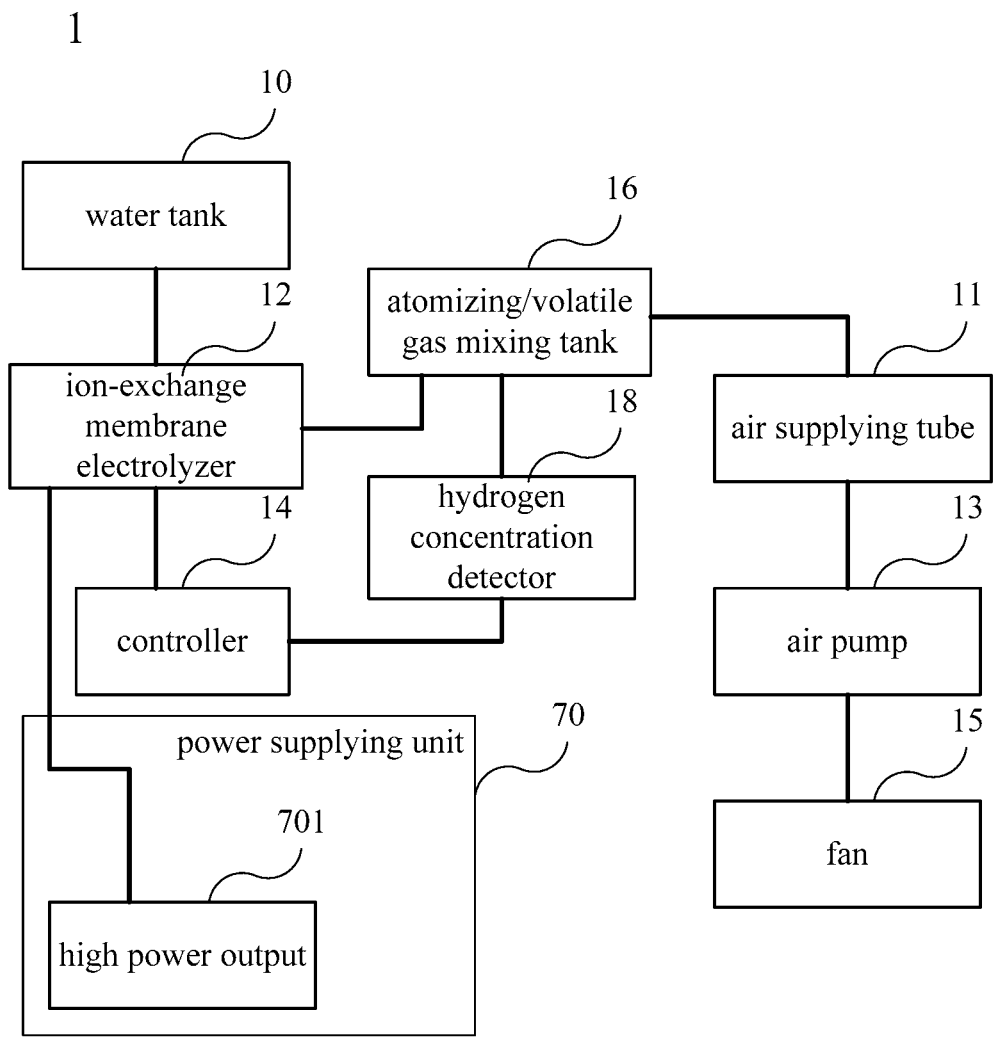
FIG. 1A is a functional block diagram illustrating a water electrolysis device according to an embodiment of the present invention.
Figure 1B:
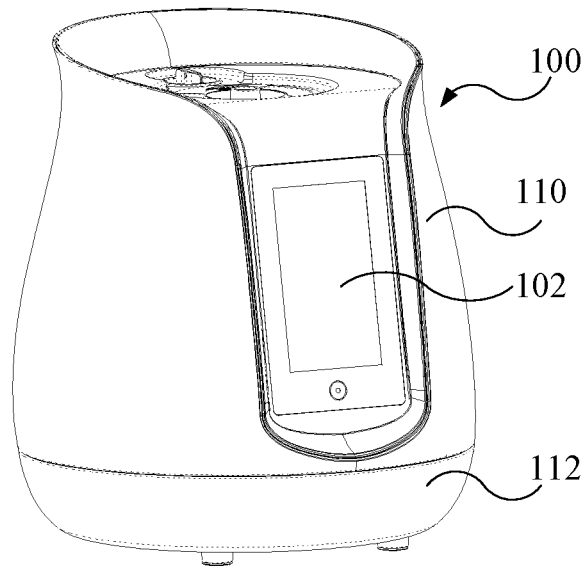
FIG. 1B is an appearance drawing illustrating the water electrolysis device according to an embodiment of the present invention.
Figure 1C:
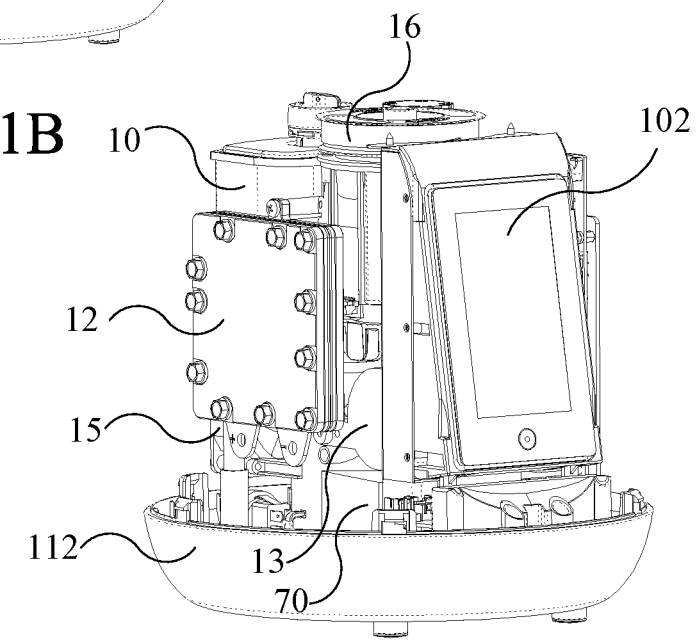
FIG. 1C is a schematic diagram of internal structure of the water electrolysis device in FIG. 1B.

Please refer to FIG. 1A to FIG. 1C. FIG. 1A is a functional block diagram illustrating a water electrolysis device 1 according to an embodiment of the present invention. FIG. 1B is an appearance drawing illustrating the water electrolysis device 1 in one embodiment of the present invention. FIG. 1C is a schematic diagram of internal structure of the water electrolysis device 1 in FIG. 1B. In this embodiment, the water electrolysis device 1 including a case 100 and an operation panel 102. The case 100 includes a side wall 110 and a base 112. The case 100 includes a water tank 10 and an ion-exchange membrane electrolyzer 12 therein. The water tank 10 is configured for providing the water for electrolyzing of the ion-exchange membrane electrolyzer 12, and is configured in a side of the case 100 opposite to the operation panel 102. The ion-exchange membrane electrolyzer 12 is configured between the operation panel 102 and the water tank 10, and in a non-central position of the case 100 for electrolyzing water to generate hydrogen gas. In one embodiment, the water can be, but not limited to, deionized water, and high-purity hydrogen gas can be prepared. In practical applications, any kind of water available can be adopted. Moreover, the present invention is not limited to the ion-exchange membrane electrolyzer; other types of electrolyzer also can be adopted in the present invention.

Each of the components disclosed in FIG. 1A is contained in a containing space of the case 100, such as the water tank 10, the ion-exchange membrane electrolyzer 12, an air pump 13, a fan 15, an atomizing/volatile gas mixing tank 16 and a power supplying unit 70, wherein the fan 15 and the water tank 10 are configured on one side opposite to the operation panel 102, and the fan 15 is configured below the water tank 10 from the perspective of FIG. 1C. A part of the air pump 13 is covered by the operation panel 102. As shown in FIG. 1B, a containing space formed by the case 100, or by the side wall 110 and the base 112, includes a bottom space and a top space, and the bottom space is larger than the top space. For example, when the principal design of the water electrolysis device 1 of the present invention is circular, as shown in FIG. 1B, the longest section length of the circular base 112, that is, the diameter, is larger than the longest section length of the top of the circular case 100, so that the bottom space is larger than the top space. The case 100 presents a design of tapering from the bottom to the top. However, the design of the present invention is not limited to the circular form. The shape of the water electrolysis device 1 can be other shapes. For example, the shape of the water electrolysis device can be ellipse, square or polygon form, as long as the bottom or the longest section length of the base 112 is larger than the longest section length of the top to conform to the design of tapering from bottom to the top. In order to arrange the containing space, the inventor places the power supplying unit 70 in the bottom of the case 100, and below the water tank 10, the ion-exchange membrane electrolyzer 12 and the air pump 13.

Figure 2A:
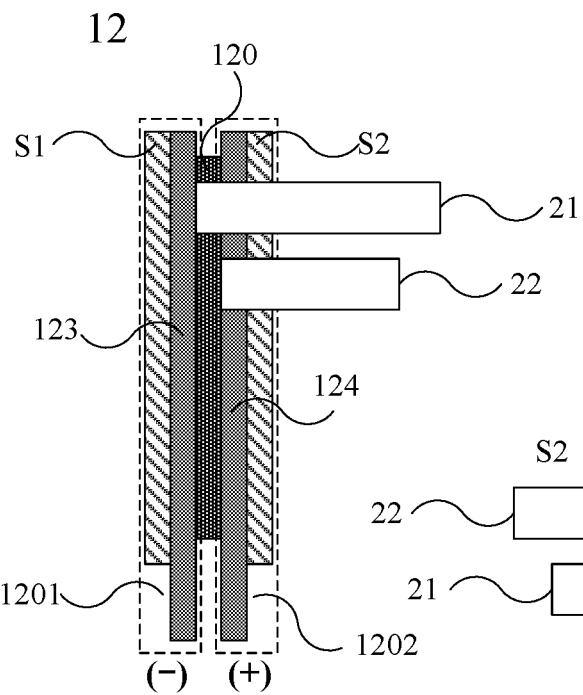
FIG. 2A is a simple sectional schematic diagram illustrating an ion-exchange membrane electrolyzer according to an embodiment of the present invention.
Figure 2B:
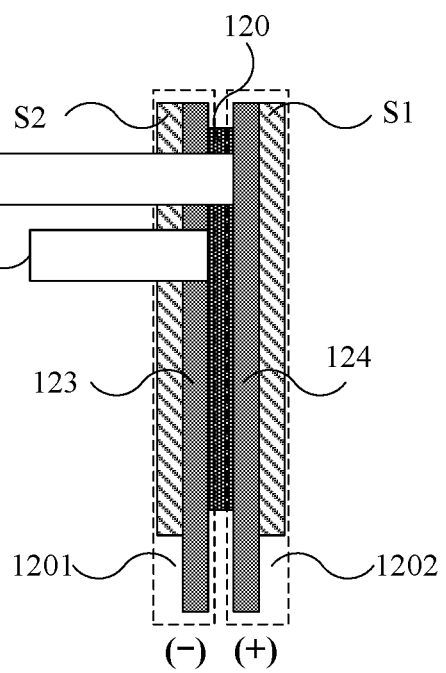
FIG. 2B is a simple sectional schematic diagram illustrating an ion-exchange membrane electrolyzer according to another embodiment of the present invention.

Please refer to FIG. 2A and FIG. 2B. FIG. 2A is a simple sectional schematic diagram illustrating the ion-exchange membrane electrolyzer 12 according to an embodiment of the present invention. FIG. 2B is a simple sectional schematic diagram illustrating the ion-exchange membrane electrolyzer 12 in another embodiment of the present invention. This paragraph will cooperate with FIG. 2A and FIG. 2B to briefly explain the main feature of the present invention. As shown in FIG. 2A, the ion-exchange membrane electrolyzer 12 substantially includes an ion-exchange membrane 120, a cathode 123, an anode 124, a first side S1, a second side S2, a hydrogen output tube 21 and an oxygen output tube 22. The ion-exchange membrane 120 is configured between the first side S1 and the second side S2. The cathode 123 is configured between the ion-exchange membrane 120 and the first side S1. The anode 124 is configured between the ion-exchange membrane 120 and the second side S2. The area where the first side S1 and the cathode 123 are located is referred as a cathode chamber 1201, and the area where the second side S2 and the anode 124 are located is referred as an anode chamber 1202. In order to express the corresponding positions of the cathode chamber 1201 and the anode chamber 1202 more clearly, the positions are indicated by broken lines in FIG. 2A. The hydrogen output tube 21 extends from the position between the ion-exchange membrane 120 and the first side S1 to the second side S2 and passes through the second side S2. The oxygen output tube 22 extends from the position between the ion-exchange membrane 120 and the second side S2 to the second side S2 and passes through the second side S2. When the ion-exchange membrane electrolyzer 12 electrolyzes water, the cathode 123 generates hydrogen gas and the anode 124 generates oxygen gas. The main feature of the present invention is that the hydrogen gas and oxygen gas generated by electrolyzing water are outputted together from the second side S2 of the ion-exchange membrane electrolyzer 12 respectively via the hydrogen output tube 21 and the oxygen output tube 22. In this embodiment, the hydrogen output tube 21 is outputted together with the oxygen output tube 22 from one side of the anode chamber 1202 of the ion-exchange membrane electrolyzer 12.

However, the positions of the hydrogen output tube 21 and the oxygen output tube 22 of the present invention are not limited to the foregoing embodiments. Please refer to FIG. 2B. The ion-exchange membrane electrolyzer 12 shown by FIG. 2B has the same components as shown by FIG. 2A. The difference is that the configured positions of the first side S1 and the second side S2 in FIG. 2B are opposite to those in FIG. 2A, so that in FIG. 2B, the anode 124 is configured between the ion-exchange membrane 120 and the first side S1, and the cathode 123 is configured between the ion-exchange membrane 120 and the second side S2. The cathode chamber 1201 includes the second side S2 and cathode 123. The anode chamber 1202 includes the first side S1 and the anode 124. The hydrogen output tube 21 extends from the position between the ion-exchange membrane 120 and the second side S2 to the second side S2 and passes through the second side S2. The oxygen output tube 22 extends from the position between the ion-exchange membrane 120 and the first side S1 to the second side S2 and passes through the second side S2. When the ion-exchange membrane electrolyzer 12 electrolyzes water, the cathode 123 generates hydrogen gas and the anode 124 generates oxygen gas. The main feature of the present invention is that the hydrogen gas and oxygen gas generated by electrolyzing water are outputted together to the second side S2 of the ion-exchange membrane electrolyzer 12 respectively via the hydrogen output tube 21 and the oxygen output tube 22. In this embodiment, the hydrogen output tube 21 is outputted together with the oxygen output tube 22 from one side of the cathode chamber 1201 of the ion-exchange membrane electrolyzer 12. That is to say, the hydrogen output tube 21 and the oxygen output tube 22 in the present invention can be configured on either side of the ion-exchange membrane electrolyzer 12 according to the practical requirement of the user.

Figure 2C:
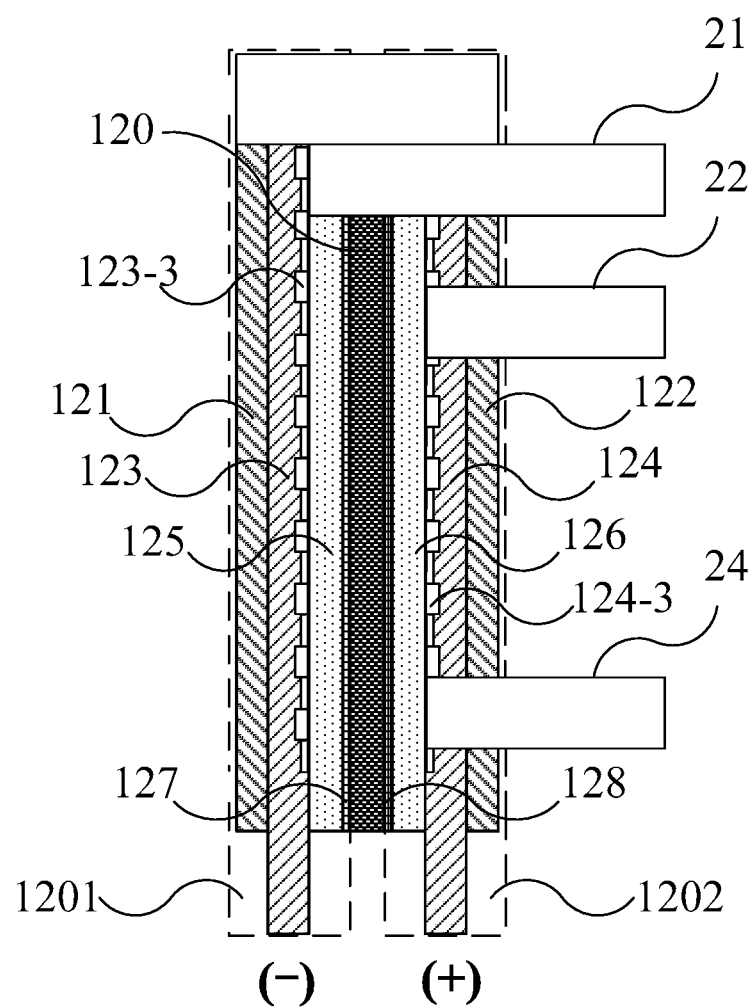
FIG. 2C is a sectional schematic diagram illustrating the ion-exchange membrane electrolyzer according to the embodiment of FIG. 2A.

Please refer to FIG. 2C. FIG. 2C is a sectional schematic diagram illustrating the ion-exchange membrane electrolyzer 12 according to the embodiment of FIG. 2A. As shown in FIG. 2C, the ion-exchange membrane electrolyzer 12 includes an ion-exchange membrane 120, a cathode chamber 1201 and an anode chamber 1202. The cathode chamber 1201 includes a cathode 123. The anode chamber 1202 includes an anode 124. The ion-exchange membrane 120 is configured between the anode chamber 1202 and the cathode chamber 1201, wherein when the ion-exchange membrane electrolyzer 12 electrolyzes water, the cathode 123 generates hydrogen gas, and the anode 124 generates oxygen gas. In one embodiment, the anode chamber 1202 is filled with water, and the water in the anode chamber 1202 can further penetrate through the ion-exchange membrane into the cathode chamber 1201. In addition, FIG. 2A to FIG. 2C are only the sectional schematic diagrams for explaining the internal structure of the ion-exchange membrane electrolyzer, but not the actual internal structure of the ion-exchange membrane electrolyzer. The blank block in FIG. 2C indicates the external case of the ion-exchange membrane electrolyzer.

As shown in FIG. 2C, the ion-exchange membrane 120 includes an ion-exchange membrane body 1203, a cathode catalytic layer 127 and an anode catalytic layer 128. The ion-exchange membrane body 1203 can be a proton exchange membrane, and preferably a Nafion membrane. The cathode catalytic layer 127 can be selected from one or a combination from a group consisting of Pt, Ir, Pd and Pt alloy powders. The anode catalytic layer 128 can be selected from one or a combination from a group consisting of Pt, Ir, Pd, Pt alloy powders and Carbon. In one embodiment, the materials of the cathode catalytic layer 127 or the anode catalytic layer 128 can be respectively configured as slurry coatings on both sides of the ion-exchange membrane to form the cathode catalytic layer 127 and the anode catalytic layer 128. In practical applications, the hydrogen gas can be generated on the catalytic layer, but not limited thereto. The hydrogen gas also can be generated on the electrode plate, or even between the ion-exchange membrane and the electrode plate. Therefore, compared with the conventional alkali-type electrolyzer, the ion-exchange membrane electrolyzer 12 used in the present invention can avoid the problems of corrosion of the tank body, environmental pollution, incomplete filtration and inhalation of the electrolyte-containing gas.

Please refer to FIG. 2A to FIG. 2C. The cathode chamber 1201 includes a cathode external plate 121, a cathode 123, a cathode sealing plate 125 and a cathode catalytic layer 127. The anode chamber 1202 includes an anode external plate 122, an anode 124, an anode sealing plate 126 and an anode catalytic layer 128. As shown in FIG. 2A, the first side S1 and the second side S2 respectively corresponds to the cathode external plate 121 and the anode external plate 122 in FIG. 2C. On the other hand, as shown in FIG. 2B, the first side S1 and the second side S2 of FIG. 2B respectively corresponds to the anode external plate 122 and the cathode external plate 121 of FIG. 2C. The ion-exchange membrane electrolyzer 12 includes a hydrogen output tube 21, an oxygen output tube 22 and a water supplying pipe 24. The oxygen output tube 22 is used for outputting oxygen gas, and the cathode output tube 21 is used for outputting hydrogen gas which is generated from the cathode chamber 1201. As shown in FIG. 2C, the hydrogen output tube 21 passes through the cathode sealing plate 125, the anode sealing plate 126, the anode 124 and the anode external plate 122 (the second side S2 in FIG. 2A) for connecting the cathode chamber 1201 and the external environment outside the ion-exchange membrane electrolyzer 12 and outputting hydrogen gas. The oxygen output tube 22 is used for outputting oxygen gas which is generated from the anode chamber 1202. The oxygen output tube 22 passes through the anode 124 and the anode external plate 122 for connecting the anode chamber 1202 and the external environment outside the ion-exchange membrane electrolyzer 12 and outputting oxygen gas. The water supplying pipe 24 passes through the anode 124 and the anode external plate 122, and is connected to the water tank 10 for guiding water from the water tank 10 to the anode chamber 1202 to replenish the water of electrolyzing of the ion-exchange membrane electrolyzer 12. The oxygen output tube 21 and the hydrogen output tube 22 are both configured on the same side of the ion-exchange membrane electrolyzer 12. In this embodiment, all of the oxygen output tube 21, the hydrogen output tube 22 and water supplying pipe 24 pass through and are configured on the anode external plate 122. However, the present invention is not limited to the aforementioned feature. For example, the oxygen output tube 21, the hydrogen output tube 22 and the water supplying pipe 24 also can pass through and be configured on the cathode external plate 121 in the similar structure, as shown in the second side S2 of FIG. 2B.

Figure 3:
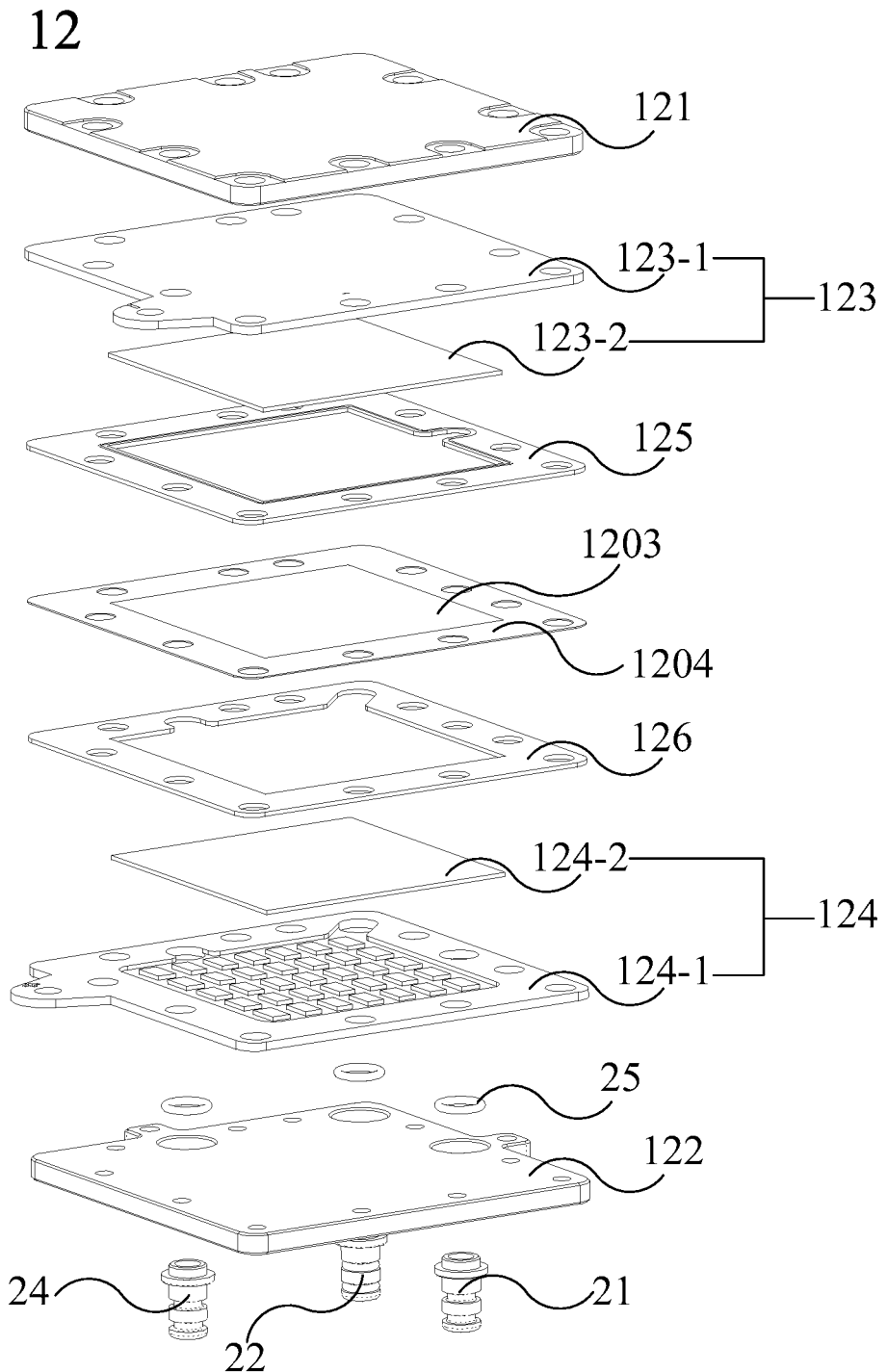
FIG. 3 is an exploded diagram illustrating an ion-exchange membrane electrolyzer according to an embodiment of the present invention.
Figure 4:
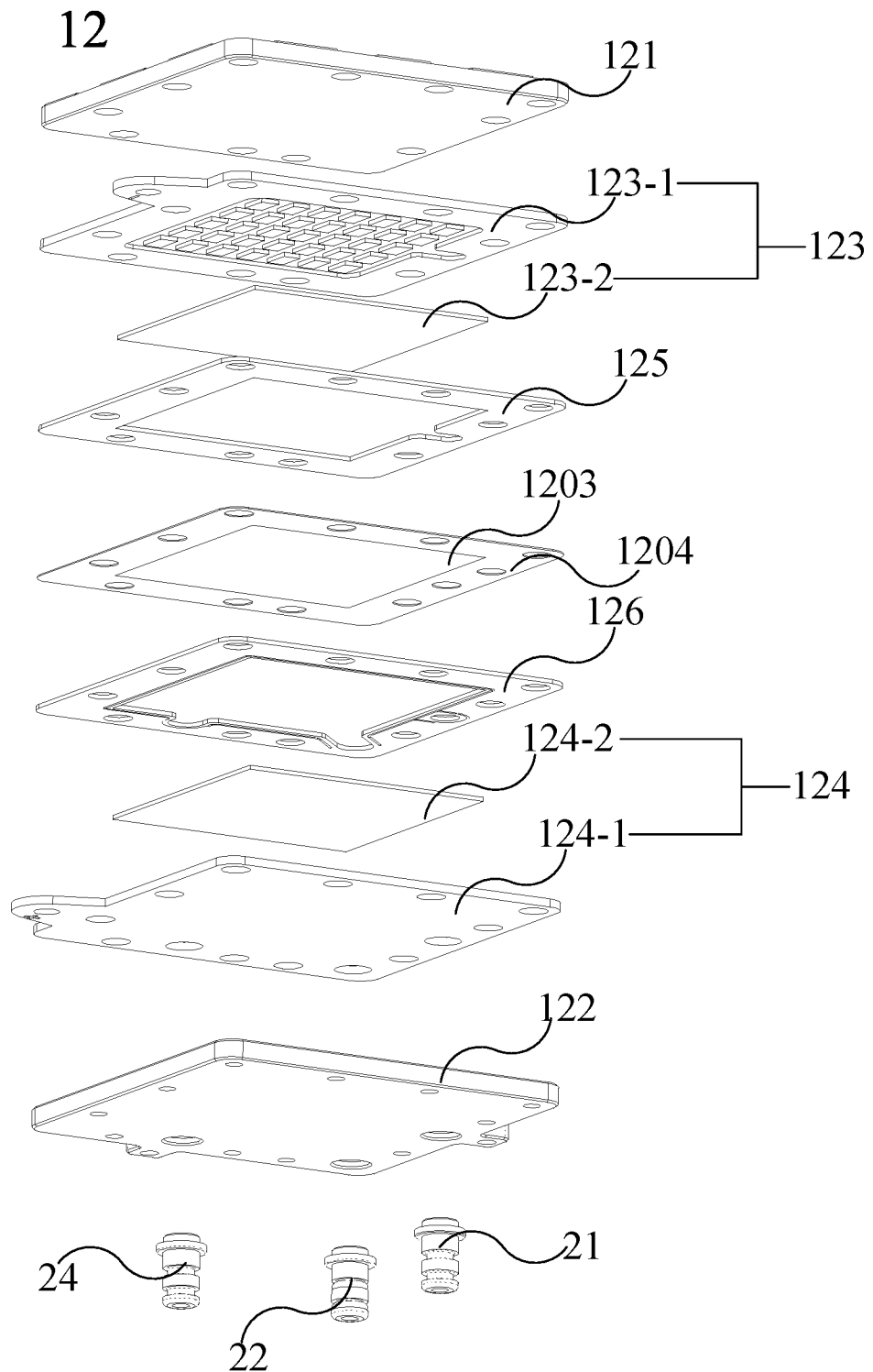
FIG. 4 is an exploded diagram illustrating the ion-exchange membrane electrolyzer in FIG. 3 from another perspective according to an embodiment of the present invention.

Please refer from FIG. 3 to FIG. 4. FIG. 3 is an exploded diagram illustrating the ion-exchange membrane electrolyzer 12 according to an embodiment of the present invention. FIG. 4 is an exploded diagram of the ion-exchange membrane electrolyzer 12 different from another perspective according to an embodiment of the present invention. The ion-exchange membrane 120 further includes an ion-exchange membrane external plate 1204 for fixing the relative positions of the ion-exchange membrane body 1203, the cathode catalytic layer 127 and the anode catalytic layer 128 in the ion-exchange membrane electrolyzer. FIG. 3 and FIG. 4 show the relationship of the positions of the components in the ion-exchange membrane electrolyzer 12 more clearly. The ion-exchange membrane electrolyzer 12 includes various components which can be assembled in the stacking sequence as shown in FIG. 3 and FIG. 4.

Please continue to refer to FIG. 3 to FIG. 4. In one embodiment, the ion-exchange membrane external plate 1204, the cathode sealing plate 125 and the anode sealing plate 126 can be arranged around the electrode plate to achieve insulation and airtightness, wherein the material of the ion-exchange membrane external plate 1204, the cathode sealing plate 125 and the anode sealing plate 126 may be silicone. However, the configuration and material of the cathode sealing plate 125 and the anode sealing plate 126 are not limited to the above embodiment. In practice, any configuration and material with insulation and airtightness effect can be adopted for the cathode sealing plate and the anode sealing plate.

As shown in FIG. 3 and FIG. 4, the hydrogen output tube 21 passes through the cathode sealing plate 125, the ion-exchange membrane external plate 1204, the anode sealing plate 126, the anode 124 and the anode external plate 122, so that the hydrogen gas generated in the cathode chamber 1201 can be outputted from the side of the anode external plate 122 via the hydrogen output tube 21 and the ion-exchange membrane external plate 1204. The oxygen output tube 22 passes through the anode 124 and the anode external plate 122, so that the oxygen gas generated in the anode chamber 1202 can be outputted from the side of the anode external plate 122 via the oxygen output tube 22. The water supplying pipe 24 passes through the anode 124 and the anode external plate 122, and connects to the water tank 10 for guiding water from the water tank 10 into the anode chamber 1202 to replenish the water of electrolyzing of the ion-exchange membrane electrolyzer 12. O-ring 25 are configured between the hydrogen output tube 21, the oxygen output tube 22 and the water supplying pipe 24 with the anode external plate 122 to seal the space between the hydrogen output tube 21, the oxygen output tube 22 and the water supplying pipe 24 with the anode external plate 122.

As shown in FIG. 3 and FIG. 4, the cathode 123 includes a cathode conductive plate 123-1 and a cathode electrode plate 123-2, and the anode 124 includes an anode conductive plate 124-1 and an anode electrode plate 124-2. In one embodiment, each electrode plate can be, but not limited to, a titanium powder die-casting sheet, and the material of each conductive plate can be, but not limited to, titanium. As shown in FIG. 3, in one embodiment, the cathode electrode plate 123-2 can be configured between the ion-exchange membrane 120 or ion-exchange membrane body 1203 and the cathode conductive plate 123-1. The anode electrode plate 124-2 can be configured between the ion-exchange membrane 120 or ion-exchange membrane body 1203 and the anode conductive plate 124-1. The ion-exchange membrane electrolyzer 12 can be connected to an outer power via the cathode conductive plate 123-1 and the anode conductive plate 124-1. In one embodiment, the anode conductive plate 124-1 (as shown in FIG. 3) and the cathode conductive plate 123-1 (as shown in FIG. 4) have flow channels respectively. When the cathode conductive plate 123-1 and the cathode electrode plate 123-2 are stacked on each other, a plurality of cathode chambers 123-3 may be formed in the cathode chamber 1201. When the anode conductive plate 124-1 and the anode electrode plate 124-2 are stacked on each other, a plurality of anode chambers 124-3 may be formed in the anode chamber 1202. The cathode chamber 123-3 and the anode chamber 124-3 can be used to circulate gas and water therein, wherein the anode chamber 124-3 is connected to the oxygen output tube 22, and the cathode chamber 123-3 is connected to the hydrogen output tube 21.

Figure 5A:
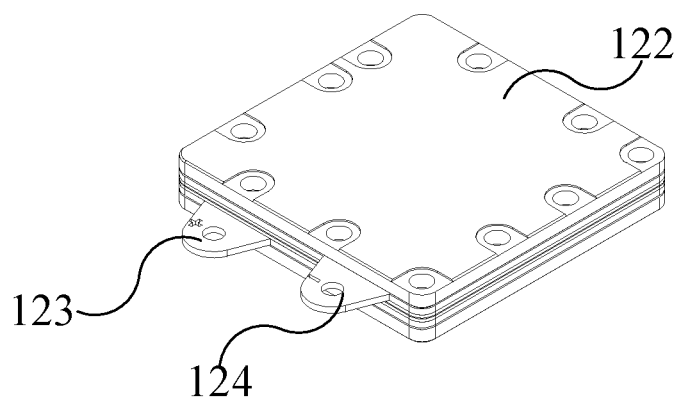
FIG. 5A and FIG. 5B are assembly diagrams illustrating the ion-exchange membrane electrolyzer in FIG. 3 from different perspectives.
Figure 5B:
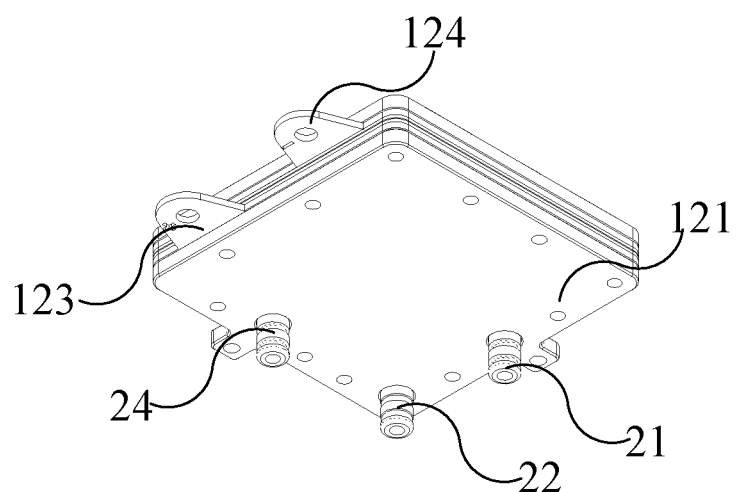

Please refer to FIG. 5A and FIG. 5B. FIG. 5A and FIG. 5B are assembly diagrams illustrating the ion-exchange membrane electrolyzer 12 in FIG. 3 from different perspectives. The cathode external plate 121 and the anode external plate 122 are configured respectively on both outer sides of the ion-exchange membrane electrolyzer 12 to fix and isolate the entire ion-exchange membrane electrolyzer 12, wherein the materials of the cathode external plate 121 and the anode external plate 122 may be stainless steel. In one embodiment, after the ion-exchange membrane electrolyzer 12 is assembled, it may be locked with a locking component (as shown in FIG. 6), but the number, type and locking way of the locking components are not limited to those shown in the figure (FIG. 6). As shown in the figure, the volume of the ion-exchange membrane electrolyzer 12 is relatively small. Therefore, the water electrolysis device is also compact in the present invention.

Please refer to FIG. 1A, FIG. 6, and FIG. 7A to FIG. 7B. FIG. 6 is an exploded diagram illustrating the water electrolysis device according to an embodiment of the present invention. FIG. 7A and FIG. 7B are the exploded diagrams and assembly diagrams illustrating the water electrolysis device in FIG. 6 from another perspective. For illustration, only necessary elements are shown in FIG. 6, FIG. 7A and FIG. 7B. The water electrolysis device 1 of the present invention also includes an air supplying tube 11, an air pump 13, a fan 15, an atomizing/volatile gas mixing tank 16, a hydrogen concentration detector 18, a controller 14, a gas-water separation tank 30 and a water level detecting device 40 in addition to the aforementioned water tank 10 and ion-exchange membrane electrolyzer 12. As shown in FIG. 6, the gas-water separation tank 30 is contained in the isolated space of the water tank 10, and its detailed structure will be described later. The water level detecting device 40 is configured for detecting the amount of water in the water tank 10. In one embodiment, the water level detecting device 40 is a capacitive water level detecting device and is configured on the outer surface of the water tank 10. The amount of water in the water tank 10 is measured by measuring the difference of capacitance between the water and the water-free area in the water tank 10.

Please refer to FIG. 6, FIG. 8A and FIG. 8B. FIG. 8A is a top view diagram illustrating the water electrolysis device according to embodiment of the present invention. FIG. 8B is a sectional view diagram illustrating the water electrolysis device along to the line D-D of FIG. 8A. The hydrogen output tube 21 of the ion-exchange membrane electrolyzer 12 is connected and communicated with the gas-water separation tank 30 via a hydrogen interface 211. The oxygen output tube 22 is connected and communicated with the water tank 10 via the oxygen interface 222 The water tank 10 includes a sterilizer 50. In this embodiment, the sterilizer 50 is a long-tube ultraviolet sterilizer which is configured in the water tank 10 away from the side where the gas-water separation tank 30 is located. The water supply pipe 24 directly communicates with the side of the water tank 10 near the sterilizer 50 via the water interface 242 to receive the sterilized water from the water tank 10 to replenish the water of electrolyzing of the ion-exchange membrane electrolyzer 12. In addition, as shown FIGS. 6, 7A, 7B, 8A, and 8B, the water electrolysis device 1 further comprises a casing module comprising the water tank 10, the hydrogen interface 211, the oxygen interface 222, the water interface 242 coupled to the casing and the water tank 10, and the air supplying tube 11. Therefore, the hydrogen interface 211 and the water interface 242 are directly coupled to the hydrogen output tube 21 and the water supplying pipe 24 of the ion-exchange membrane electrolyzer 12 without extra pipeline connection to save the space in the water electrolysis device.

The gas-water separation tank 30 includes a spring valve 32, a bobber 34 and a hydrogen discharge tube 36. The hydrogen gas generated by the electrolysis of the ion-exchange membrane electrolyzer 12 is guided to the gas-water separation tank 30 via the hydrogen output tube 21 and the hydrogen interface 211. When the hydrogen gas in the gas-water separation tank 30 accumulates to a certain extent, the spring valve 32 will be opened due to the hydrogen gas pressure and allow hydrogen to be discharged to the filter 60 via the hydrogen discharge tube 36 to filter impurities in the hydrogen gas. Furthermore, when the hydrogen gas is outputted from the ion-exchange membrane electrolyzer 12, a small amount of residual electrolyzed water may be contained in the hydrogen gas, and the residual electrolyzed water may accumulate in the gas-water separation tank 30 to form liquid water, so as to cause bobber 34 to float due to the accumulated liquid water. At this time, a drain port (not shown) covered by the bobber 34 will be opened, and the accumulated liquid water will be discharged into the water tank 10 through the drain port for recycling.

The oxygen gas generated by the electrolysis is directly discharged to the water tank 10 via the oxygen output tube 22 and the oxygen interface 222. The oxygen gas will be discharged to the atmospheric environment from the upper portion of the water tank 10. When the oxygen gas is outputted from the ion-exchange membrane electrolyzer 12, a small amount of residual electrolyzed water may be contained in the oxygen gas, and the residual electrolyzed water will be directly discharged into the water tank 10 for recycling.

Please refer to FIG. 7A, FIG. 7B, FIG. 8A and FIG. 9 together. FIG. 9 is a sectional view diagram illustrating the water electrolysis device along the line D-D of the FIG. 8A. As mentioned in the previous paragraph, the hydrogen gas is discharged to the filter 60 via the hydrogen discharge tube 36, and then a filter core 602 of the filter 60 filters the impurities in the hydrogen gas. The filtered hydrogen gas is further guided into the air supplying tube 11 for dilution and then guided into the atomizing/volatile gas mixing tank 16. The air supplying tube 11 is connected to the filter 60 to receive the filtered hydrogen gas, and the air supplying tube 11 is connected to the air pump 13. The fan 15 draws air from the external environment into the water electrolysis device 1 to dilute the hydrogen gas in the air supplying tube 11. The case 100 is set with a plurality of small holes. The fan 15 draws air from the external environment into the water electrolysis device 1 through the small holes on the case 100. The drawn air is guided into the air supplying tube 11 by the air pump 13. In this embodiment, the air pump 13 is a vortex fan, and the air drawn by the fan 15 is drawn into the air pump 13 through a drawing port 134 of the air pump 13, so as to guide air into the air supplying tube 11. As shown in FIG. 7B and FIG. 9, a duct 132 of the air pump 13 is connected with an air supplying interface 112 of the air supplying tube 11. The air supplying tube 11 has a first flow direction D1, and the air supplying interface 112 has a second flow direction D2. The first flow direction D1 points to the atomizing/volatile gas mixing tank 16, as indicated by the arrow on the indication line representing the first flow direction D1, and the arrow on the indication line also points to the position above the water electrolysis device. The second flow direction D2 points to the air supply tube 11, as indicated by an arrow on the indication line representing the second flow direction D2, so that the air from the duct 132 through the air supplying interface 112 is guided into the air supplying tube 11. A lead angle A is formed between the first flow direction D1 and the second flow direction D2. The lead angle A is an acute angle of less than 90 degrees, and preferably, between 25 to 45 degrees. At the connecting position of the air supplying tube 11 and the air supplying interface 112 where the lead angle A is located, the shape of the connecting position can be made as an arc lead angle. The air in the duct 132 and the air supplying interface 112 may be guided into the air supplying tube 11 by the design of the lead angle A to dilute the hydrogen gas in the atomizing/volatile gas mixing tank 16.

Please continue to refer to FIG. 9. The atomizing/volatile gas mixing tank 16 is connected with the air supplying tube 11, and receives the filtered and diluted hydrogen gas to generate an atomizing gas and mix it with the hydrogen gas to form a health gas, wherein the atomizing gas is one or a combination selected from a group consisting of water vapor, atomizing potions and volatile essential oil. The atomizing/volatile gas mixing tank 16 includes an oscillator 162. The oscillator 162 atomizes water, atomizing potions or volatile essential oil added to the atomizing/volatile gas mixing tank 16 by oscillation to generate the atomizing gas, and then mixes the hydrogen gas with the atomizing gas to form a health gas. The atomizing/volatile gas mixing tank 16 can be selectively opened or closed according to user's requirements. That is to say, the atomizing/volatile gas mixing tank 16 can be activated by actuating the oscillator to provide the hydrogen gas mixing with the atomizing gas for the user, or the atomizing/volatile gas mixing tank 16 can be closed by stopping the oscillator to provide the filtered and diluted hydrogen without mixing with the atomizing gas for the user. The means for user to inhale the filtered and diluted hydrogen or the health gas includes that the atomizing/volatile gas mixing tank 16 directly releases the hydrogen or health gas into the atmosphere, or provides for the user inhaling via a conduit and a mask.

The hydrogen concentration detector 18 is connected with the atomizing/volatile gas mixing tank 16 to detect the hydrogen concentration in the atomizing/volatile gas mixing tank 16. The controller 14 is connected to the hydrogen concentration detector 18, the air pump 13 and the ion-exchange membrane electrolyzer 12. In one embodiment, the hydrogen concentration detector 18 can be connected to the hydrogen output tube 21 or the hydrogen interface 211 to detect the volume concentration of the hydrogen gas which is outputted from the ion-exchange membrane electrolyzer 12 to the atomizing/volatile gas mixing tank 16. The hydrogen concentration detector 18 detects whether the hydrogen volume concentration is within a range from a first predetermined value to a second predetermined value. For example, the first predetermined value is 4%, the second predetermined value is 6%, and the hydrogen concentration detected by the hydrogen concentration detector 18 ranges from 4% to 6%. The first predetermined value and the second predetermined value can be adjusted through the operation panel 102 according to the requirement of the user. In this embodiment, when the hydrogen concentration detector 18 detects that the volume of hydrogen gas in the hydrogen output tube 21 or the hydrogen interface 211 is higher than the first predetermined value by 4%, a first warning signal is generated to the controller 14. When the controller 14 receives the first warning signal, a start command is generated to the air pump 13 to start up the air pump 13 to draw air into the air supplying tube 11 to dilute the hydrogen gas in the air supplying tube 11. When the hydrogen concentration detector 18 detects that the volume of hydrogen gas in the hydrogen output tube 21 or the hydrogen interface 211 is higher than the second predetermined value by 6%, a second warning signal is generated to the controller 14. When the controller 14 receives the second warning signal, a stop command is generated to stop the ion-exchange membrane electrolyzer 12 by the means such as cutting off the power input to the ion-exchange membrane electrolyzer 12, and then the gas explosion due to the excessive hydrogen concentration can be avoided, thereby improving the overall safety.

Please refer to FIG. 10. FIG. 10 is a sectional view diagram illustrating the water electrolysis device 1 according to another embodiment of the present invention. In another embodiment of present invention, a preheating water tank 17 is further connected between the water tank 10 and the ion-exchange membrane electrolyzer 12. The preheating water tank 17 is substantially cylindrical or circular. Although the preheating water tank 17 is larger than the water tank 10 in FIG. 10, in other embodiments, the volume of the preheating water tank 17 can be smaller than that of the water tank 10. The preheating water tank 17 includes a preheating water tank water filling port 172 which is connected to the lower port 10-2 of the water tank 10, an electrolyzed water inlet 174 which is connected to the water supplying pipe 24 of the ion-exchange membrane electrolyzer 12, an oxygen receiving tube 176 which is connected to the oxygen output tube 22 and an oxygen discharge tube 178 which is connected to the upper port 10-1 of the water tank 10. The preheating water tank 17 is configured between the water tank 10 and the ion-exchange membrane electrolyzer 12. The electrolyzed water in the water tank 10 flows into the preheating water tank 17 via the lower port 10-2 first, and then flows into the ion-exchange membrane electrolyzer 12 through the electrolyzed water inlet 174 for electrolysis. The oxygen gas generated during the process of electrolyzing water and a portion of the residual electrolyzed water are discharged into the preheating water tank 17 via the oxygen receiving tube 176, wherein the part of the residual electrolyzed water will remain in the preheating water tank 17. The oxygen gas generated by the electrolysis will be discharged to the water tank 10 through the upper port 10-1 via the oxygen discharge tube 178, and then discharged to the outside of the water electrolysis device.

Due to the process of electrolyzing water, the temperature of the ion-exchange membrane electrolyzer 12 will increase, and the temperature of the electrolyzed water is also related to the electrolysis efficiency. The temperature of electrolyzed water about 55 to 65° C. can improve the electrolysis efficiency. Thus, the preheating water tank 17 of the present invention recovers the higher temperature residual electrolyzed water discharged from the oxygen output tube 22 of the ion-exchange membrane electrolyzer 12 to preheat the electrolyzed water entering the ion-exchange membrane electrolyzer 12 in the preheating water tank 17 to an appropriate temperature, for example, between 55 and 65° C. In order to control the temperature of the electrolyzed water in the preheating water tank 17 to be maintained between 55 and 65° C., the preheating water tank 17 further includes a plurality of cooling fins 171 and a second fan 173. The plurality of cooling fins 171 are configured on the outer wall of the preheating water tank 17 in a radial pattern. The second fan 173 is configured at one end of the preheating water tank 17 and is matched with the plurality of cooling fins 171 to dissipate the preheating water tank 17 by forced convection. For the sake of simplicity, the cooling fins 171 are drawn only on a part of the outer wall of the preheating water tank 17. In other embodiments, the cooling fins 171 can be distributed on the whole outer wall of the preheating water tank 17.

One of the purposes of the present invention is to reduce the volume of the water electrolysis device and the noise while maintaining sufficient hydrogen production, so that the user can use it during sleeping. Therefore, the applicant firstly reduced the volume of the water electrolysis device as the main purpose. In one embodiment, the water electrolysis device of the present case is roughly cylindrical. The longest section length at the bottom, that is, the diameter, is at least 200 mm, and the height of the device is up to 270 mm, so the volume is at most about 8,500 cubic centimeters, or 8.5 liters. However, the shape of the water electrolysis device of the present invention is not limited to the cylindrical type, and the shape of the water electrolysis device can be other shapes. For example, the water electrolysis device can be elliptical, square or polygonal, as long as the bottom or the longest sectional side of the base 112 is longer than the longest sectional side of the top to conform to the design of tapering from the bottom to the top. The effective use of the containing space defined by the case of the water electrolysis device is utilized as much as possible to maintain sufficient hydrogen production for the user. For example, the water electrolysis device has a total of six output settings for the hydrogen generating rates, including the hydrogen generating rate for the water electrolysis device outputting the health gas which mixes the air, the hydrogen gas and the atomizing gas: 120 ml/min, 240 ml/min, 360 ml/min, respectively corresponding to three corresponding settings of the health gas outputting rate of the water electrolysis device: 2 L/min, 4 L/min and 6 L/min; and including the hydrogen generating rates for the water electrolysis device outputting the pure hydrogen gas: 400 ml/min, 500 ml/min, 600 ml/min. The user is allowed to adjust the hydrogen generation rate of the water electrolysis device 1 and the type of gas outputted through the operation panel. This device also reduces the noise, so that the user can place the present invention close to the user's head while sleeping.

Please refer to FIG. 1A. In one embodiment, the present invention provides a water electrolysis device 1 including a power supplying unit 70 for converting supply mains to output 240 watts of direct current to supply power of the water electrolysis device 1. The power supplying unit 70 includes a high power output 701 and a low power output. The high power output 701 is connected to the ion-exchange membrane electrolyzer 12 to supply the electric power required for the electrolysis reaction. The low power output is suitable for supplying electrical power to other non-electrolysis components in the water electrolysis device 1, such as the air pump 13, the controller 14, the fan 15, and the hydrogen concentration detector 18. In order to simplify the content of the drawing, only the power supplying unit 70 and the high power output 701 are depicted in FIG. 1A. One of ordinary skills in the art should be able to know the configuration of the low power output in the water electrolysis device to supply the power required for the operation of the water electrolysis device.

In the 240 watts of direct current supplied by the power supplying unit 70, 172 watts are outputted from the high power output 701 to the ion-exchange membrane electrolyzer 12. The high power output 701 outputs a first voltage and a first current, wherein the range of the first voltage is between 3 volts and 6.3 volts and the output of the first current is in a range from 10 amps to 27.3 amps. The low power output outputs 60 watts of direct current to supply the power required to operate the water electrolysis device. The low power output outputs a second voltage and a second current, wherein the second voltage is a DC voltage of 24 volts, and a second current is up to 2.5 amps. In another one embodiment, the second voltage can also be reduced down from 24 volts to 5 volts and output a second current up to 0.5 amps. Comparing the power parameters outputted by the high power output with the low power output, the first voltage is lower than the second voltage, but the first current is higher than the second current. Therefore, the high power output outputs high-current low-voltage DC power, and the low power output outputs low-current high-voltage DC power.

With the examples and explanations mentioned above, the present invention provides a water electrolysis device including an ion-exchange membrane electrolyzer with the hydrogen gas and the oxygen gas outputted from the same side, an air supplying tube, an air pump, and an atomizing/volatile gas mixing tank. The ion-exchange membrane electrolyzer electrolyzes water to generate hydrogen gas. After the hydrogen gas is inputted to the air supplying tube, the air pump draws in air, and the air is unidirectionally inputted into the air supplying tube through a air supplying interface having a lead angle with the air supplying tube to dilute the hydrogen gas in the air supplying tube, and the air supplying tube then introduces the diluted hydrogen into the atomizing/volatile gas mixing tank and mixes with an atomizing gas for the user.

Through the ion-exchange membrane electrolyzer with the hydrogen gas and the oxygen gas outputted from the same side, and the water tank, the gas-water separation tank, and the air supplying tube configured in a case within a defined volume, the water electrolysis device of the present invention employs the containing space in the case as much as possible while maintaining sufficient hydrogen production, and the fan and the air pump of water electrolysis device are also based on low noise. Therefore, this present invention actually provides a water electrolysis device with effective space arrangement, small volume and low noise, and suitable for placing around the user.

The features and spirits of the present invention are hopefully described more clearly by the above detailed description of the preferred embodiments, and the scope of the present invention is not limited by the preferred embodiments disclosed above. On the contrary, the purpose is to cover a variety of changes and equivalence arrangements within the scope of the patent application to be applied for by the creative institute. Although the present invention has been disclosed in the above embodiments, it is not intended to limit the present invention, and anyone skilled in the art can make various changes and refinements without departing from the spirit and scope of the present invention. Therefore, the scope of protection of this present invention is subject to the definition of the scope of the patent application attached.

What is claimed is:

1. A water electrolysis device, comprising:
    a case having a containing space;
    a power supplying unit configured in the containing space of the case for supplying power of the water electrolysis device, wherein the power supplying unit comprises a high power output and a low power output;
    an electrolyzer configured in the case and electrically coupled to the high power output of the power supplying unit, the electrolyzer generating hydrogen gas and an anode generating oxygen gas during electrolyzing water;
    a casing module configured in the case and coupled to the electrolyzer, the casing module comprising a water tank configured to accommodating the water for electrolyzing-casing module further comprising a hydrogen interface and a water interface to be directly coupled to the electrolyzer without extra pipeline connection to save the space in the water electrolysis device, to receive the hydrogen gas generated by the electrolyzer via the hydrogen interface, and to replenish water from the water tank to the electrolyzer via the water interface.

2. The water electrolysis device of claim 1, wherein the electrolyzer further comprises an anode chamber, the anode chamber comprises the anode, an anode sealing plate and an anode external plate, and the anode further comprises an anode conductive plate, the anode is coupled to the anode sealing plate and the anode external plate.

3. The water electrolysis device of claim 2, wherein the electrolyzer comprises a cathode chamber; the cathode chamber comprises the cathode, a cathode sealing plate and a cathode external plate, and the cathode further comprises a cathode conductive plate, the cathode is coupled to the cathode sealing plate and the cathode external plate.

4. The water electrolysis device of claim 2, wherein the electrolyzer further comprises a water supplying pipe configured to pass through the anode external plate, the anode conductive plate and the anode sealing plate to connect the anode chamber and the water tank; water from the water tank flows into the anode chamber through the water supplying pipe to replenish water in the anode chamber.

5. The water electrolysis device of claim 1, wherein the casing module further comprises a gas supplying tube with a gas supplying interface to receive the hydrogen gas, and the water electrolysis device further comprises a pump and a fan coupled to the pump, the pump is electrically coupled to the low power output of the power supplying unit and coupled to the gas supplying interface of the gas supplying tube, the fan is configured to draw the gas from the environment outside the water electrolysis device such that the pump guiding the gas into the gas supplying tube to dilute the hydrogen gas in the gas supplying tube, wherein the gas supplying tube is connected to a hydrogen output tube of the electrolyzer via the hydrogen interface to receive the hydrogen gas.

6. The water electrolysis device of claim 5, further comprising an atomizing/volatile gas mixing tank connected to the gas supplying tube and receiving the diluted hydrogen gas, and the atomizing/volatile gas mixing tank selectively generating an atomizing gas and mixing it with the hydrogen gas to form a health gas, wherein the atomizing gas is water vapor, atomizing potions or volatile essential oil.

7. The water electrolysis device of claim 5, wherein a lead angle between the gas supplying interface and the gas supplying tube is less than 90 degrees, the lead angle is formed at a connecting position of the gas supplying tube and the gas supplying interface, and the connecting position forms a shape of an arc between the gas supplying tube and the gas supplying interface.

8. The water electrolysis device of claim 7, wherein the gas supplying tube has a first flow direction, the gas supplying interface has a second flow direction, the first flow direction points to the upper portion of the water electrolysis device, the second flow direction points to the gas supplying tube, the lead angle is formed between the first flow direction and the second flow direction, the lead angle is between 25 to 45 degrees, and-the connecting position forming the lead angle forms a shape of an arc between the gas supplying tube and the gas supplying interface.

9. The water electrolysis device of claim 5, further comprising:
a hydrogen concentration detector, wherein the hydrogen concentration detector generating a first warning signal when the detected volume concentration of the hydrogen is higher than a first predetermined value; and
a controller coupled to the hydrogen concentration detector, and generating a start command to start up the pump when receiving the first warning signal, wherein the first predetermined value is 4%.

10. The water electrolysis device of claim 1, further comprising:
a hydrogen concentration detector, wherein the hydrogen concentration detector generates a second warning signal when the hydrogen concentration is higher than a second predetermined value; and
a controller coupled to the hydrogen concentration detector and generating a stop command to stop the electrolyzer when receiving the second warning signal, wherein the second predetermined value is 6%.

11. The water electrolysis device of claim 1, wherein the casing module further comprises an oxygen interface, the electrolyzer further comprises a hydrogen output tube for coupling to the hydrogen interface and outputting the hydrogen gas to the hydrogen interface, and an oxygen output tube for coupling to the oxygen interface and outputting the oxygen gas to the oxygen interface, the hydrogen output tube and the oxygen output tube extend outward from the electrolyzer.

12. The water electrolysis device of claim 1, further comprising a water level detecting device configured to detect the amount of water in the water tank.

13. The water electrolysis device of claim 1, wherein the volume of the water electrolysis device is less than 8.5L, and a hydrogen generating rate of the water electrolysis device is located in a range between 120 ml/min and 600 ml/min.

14. A water electrolysis device, comprising:
a case comprising a base, a side wall and a containing space;
a power supplying unit configured in the containing space of the case and electrically connected to the water electrolysis device, wherein the power supplying unit comprises a high power output and a low power output;
a casing module configured in the case, the casing module comprising a water tank, a hydrogen interface and a water interface, wherein the water tank is configured for accommodating water;
an electrolyzer configured in the case, the electrolyzer coupled to the casing module and electrically coupled to the high power output of the power supplying unit, the electrolyzer comprising a first side, a second side, an ion-exchange membrane, a cathode, an anode, a hydrogen output tube, and a water supplying pipe coupled to the water tank and configured to receive the water via the water interface, the ion-exchange membrane being configured between the anode and the cathode; wherein when the electrolyzer electrolyzes water, the cathode generates hydrogen gas and the anode generates oxygen gas; the hydrogen output tube is configured to output the hydrogen gas to the casing module via the hydrogen interface wherein the hydrogen output tube and the water supplying pipe extend outward from the electrolyzer to be coupled to the hydrogen interface and the water interface without extra pipeline connection to save the space in the water electrolysis device; and
an atomizing/volatile gas mixing tank coupled to the low power output of the power supplying unit, the atomizing/volatile gas mixing tank selectively generating an atomizing gas and mixing it with the hydrogen gas to form a health gas, wherein the atomizing gas is water vapor, atomizing potions or volatile essential oil.

15. The water electrolysis device of claim 14, wherein the anode is configured between the ion-exchange membrane and the second side; the cathode is configured between the ion-exchange membrane and the first side; the electrolyzer further comprises an oxygen output tube extending from the position between the ion-exchange membrane and the second side to the second side and passing through the second side; and the hydrogen output tube extends from the position between the ion-exchange membrane and the first side to the second side and passes through the second side.

16. The water electrolysis device of claim 14, wherein the anode is configured between the ion-exchange membrane and the first side; the cathode is configured between the ion-exchange membrane and the second side; the hydrogen output tube extends from the position between the ion exchange membrane and the second side to the second side and passes through the second side; and the electrolyzer further comprises an oxygen output tube extending from the position between the ion exchange membrane and the first side to the second side and passing through the second side.

17. The water electrolysis device of claim 14, wherein the high power output outputs a first voltage and a first current; the low power output outputs a second voltage and a second current; the first voltage is less than the second voltage; and the first current is greater than the second current.

18. The water electrolysis device of claim 14, wherein the first side faces the side wall, the electrolyzer further comprises an oxygen output tube to output the oxygen gas, the hydrogen output tube and the oxygen output tube are positioned on the second side of the ion-exchange membrane electrolyzer.

* * * * *

UNITED STATES PATENT AND TRADEMARK OFFICE
CERTIFICATE OF CORRECTION

PATENT NO. : 11,186,914 B2
APPLICATION NO. : 16/108729
DATED : November 30, 2021
INVENTOR(S) : Hsin-Yung Lin It is certified that error appears in the above-identified patent and that said Letters Patent is hereby corrected as shown below:

In the Claims

Column 16, Line 23, cancel the text beginning with "a casing module configured in the case and coupled to the electrolyzer," to and ending "the water interface." In Column 16, Line 32, insert the following text:
--a casing module configured in the case and coupled to the electrolyzer, the casing module comprising a water tank configured to accommodate the water for electrolyzing, the casing module further comprising a hydrogen interface and a water interface to be directly coupled to the electrolyzer without extra pipeline connection to save the space in the water electrolysis device, to receive the hydrogen gas generated by the electrolyzer via the hydrogen interface, and to replenish water from the water tank to the electrolyzer via the water interface.--

Signed and Sealed this
Twenty-sixth Day of July, 2022

Katherine Kelly Vidal
*Director of the United States Patent and Trademark Office*